United States Patent [19]

Zelman

[11] 4,303,068
[45] Dec. 1, 1981

[54] METHOD AND APPARATUS FOR SINGLE PASS HEMODIALYSIS WITH HIGH FLUX MEMBRANES AND CONTROLLED ULTRAFILTRATION

[75] Inventor: D. Allen Zelman, Troy, N.Y.

[73] Assignee: Rensselaer Polythechnic Institute, Troy, N.Y.

[21] Appl. No.: 882,111

[22] Filed: Feb. 28, 1978

[51] Int. Cl.³ .................... B01D 13/00; B01D 31/00
[52] U.S. Cl. ............................. 128/214 B; 210/637; 210/646; 210/137; 210/321.3
[58] Field of Search ................. 210/22, 23 F, 90, 137, 210/321 B, 321 UT, 646, 637, 650, 321.3, 647, 741; 128/214 B, 214 E

[56] References Cited

U.S. PATENT DOCUMENTS

| | | | |
|---|---|---|---|
| 2,365,457 | 12/1944 | Daniel | 210/8.5 |
| 3,515,275 | 6/1970 | Bowman | 210/22 |
| 3,585,131 | 6/1971 | Esmond | 210/321 |
| 3,598,727 | 8/1971 | Willock | 210/22 |
| 3,619,423 | 11/1971 | Galletti et al. | 210/22 |
| 3,795,318 | 3/1974 | Crane et al. | 210/321 |
| 3,864,248 | 2/1975 | Granger et al. | 210/19 |
| 3,926,797 | 12/1975 | Gigov et al. | 210/22 |
| 3,946,731 | 3/1976 | Lichtenstein | 128/214 R |
| 4,013,564 | 3/1977 | Nose | 210/434 |

FOREIGN PATENT DOCUMENTS 2334230 1/1975 Fed. Rep. of Germany .... 210/23 F

OTHER PUBLICATIONS

"Measurement of the Transmittance Coefficient Spectrum ... " Green et al., Transactions A.S.A.I.O. vol. 22, 1976, pp. 627–633.

"Response to rapid removal of I.M. Weight Solutes in Uremic Man", Silverstein et al., Transactions A.S.A.I.O., vol. 20, 1974, pp. 614–621.

Primary Examiner—Charles N. Hart
Assistant Examiner—David R. Sadowski
Attorney, Agent, or Firm—Holman & Stern

[57] ABSTRACT

Disclosed is a method of hemodialysis and a modification for existing hemodialyzers to facilitate use of the method. A highly porous membrane is utilized in a single pass hemodialysis system. The membrane is freely supported, such that it distends in use to maintain a constant transmembrane pressure over its entire surface. The modification to existing dialyzers includes the use of a highly porous membrane, in combination with a transmembrane pressure sensor, which controls the dialysate output flow to maintain a precise transmembrane pressure.

5 Claims, 2 Drawing Figures

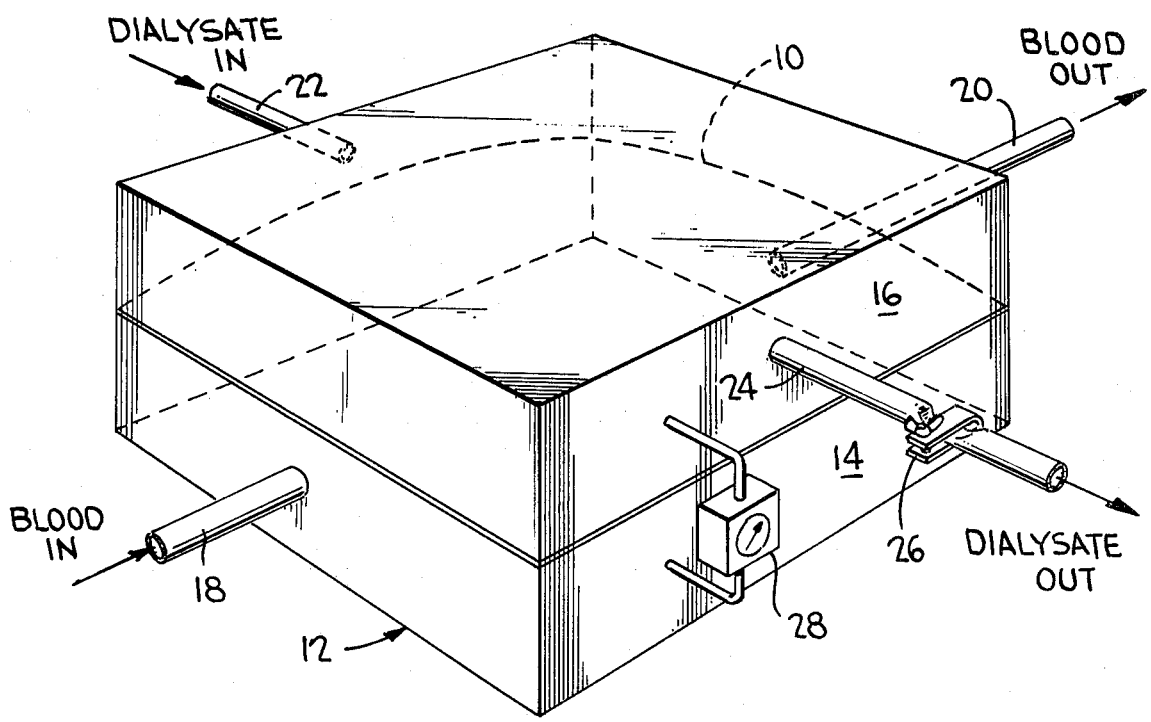
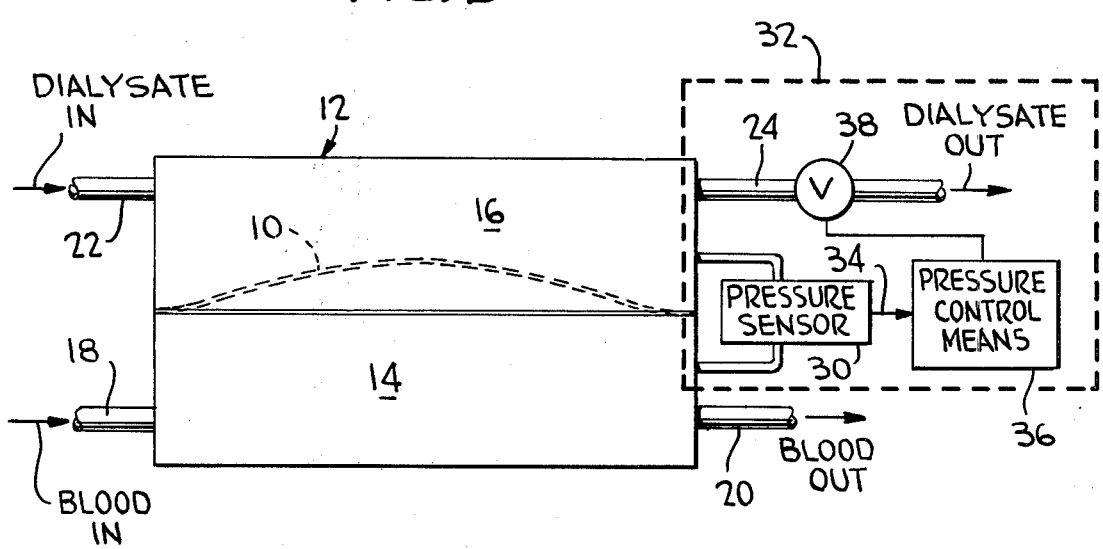

METHOD AND APPARATUS FOR SINGLE PASS HEMODIALYSIS WITH HIGH FLUX MEMBRANES AND CONTROLLED ULTRAFILTRATION

BACKGROUND OF THE INVENTION

The present invention relates to artificial kidneys which perform the four functions of the human kidney. It maintains a water balance, acid-base balance, electrolyte balance, and removes nitrogeneous wastes, such as urea and creatinine. All of these functions generally involve the transfer of relatively small molecules having a molecular weight of less than 160 daltons.

It has been found that with extended dialysis, patients who have these molecules maintained at physiologically normal levels become afflicted with neuropathy, a nervous system disorder associated with kidney failure. It is believed that there are uremotoxins having molecular weights between 300 and 2000 daltons, which may be responsible for the illnesses. This range of molecules, the so-called "middle molecules", are generally not removed in significant quantities in prior art dialyzing techniques. Previously, low flux membranes, having ultrafiltration coefficients of less than 20 ml $m^{-2}$ $hr^{-1}$ $mmHg^{-1}$ and reflection coefficients of about zero for solutes up to a molecular weight of 300 daltons, were utilized with transmembrane pressures of 50 mmHg or greater. The relative low porosity of the low flux membrane limited the ultrafiltration (water loss from the patient's blood) to acceptable levels. The high transmembrane pressure was necessary in order to achieve a reasonable level of dialysis in the single pass systems.

One alternate approach is to utilize a closed loop dialyzing system with a high flux membrane, having an ultrafiltration coefficient of at least 20 ml $m^{-2}$ $hr^{-1}$ $mmHg^{-1}$ and reflection coefficients of about zero for solutes up to a molecular weight of 2000 daltons. Because the dialysate has a fixed volume which is merely recirculated past the dialyzing membrane, and the dialysate is relatively incompressible, there will, of necessity, be little or no ultrafiltration across the dialyzing membrane. Unfortunately, because the fixed volume (generally 70 liters) of the dialysate is not much larger than the patient's "fluid compartment" (the volume of cellular and blood liquid which retains the uremotoxins, in a human about 40 liters), the final concentration of uremotoxins, if a complete concentration balance were obtained between the patient and the dialysate, will be relatively high. Furthermore, because a patient is on a dialysis machine for a relatively short period of time, the solutes never equilibrate and, thus even higher levels of uremotoxins remain in the patient after dialysis. Although this system has the capability for removing some "middle molecules" while controlling ultrafiltration, the system has a very low efficiency for the removal of the more conventional small molecular weight solutes.

Clearly, if a high flux membrane were utilized in a conventional open loop dialyzer, with conventional transmembrane pressures, on the order of 50 mmHg, an excessively high ultrafiltration rate would result, preventing the patient from being connected to the dialyzer for the required period of time.

SUMMARY OF THE INVENTION

In view of the above, it is an object of the present invention to provide a method of operation which will permit removal of "middle molecules", the conventional small solutes, and at the same time, have a very low ultrafiltration rate.

It is a further object of the present invention to provide a modification for existing dialyzers to permit removal of "middle molecules", as well as a high efficiency for the removal of small solutes, and effective control of ultrafiltration.

The above and other objects are achieved in the method of operating a single pass dialyzer with a high flux membrane at a very low transmembrane pressure. In a preferred embodiment, transmembrane pressure on a distensible membrane is regulated by controlling the output flow of dialysate, such that transmembrane pressure is very low throughout the dialyzer.

A modification to existing systems requires only a differential pressure sensor for sensing transmembrane pressure and a pressure control means responsive to the sensor which has the effect of regulating transmembrane pressure in a single pass dialyzing system.

BRIEF DESCRIPTION OF THE DRAWINGS

These and other objects and advantages of the present invention will become more apparent by referring to the accompanying drawings, in which:

FIG. 1 is a perspective view of a single pass dialyzer operating in the cross-current mode;

FIG. 2 is a cross-sectional view of a modified dialyzer operating in the co-current mode.

DETAILED DESCRIPTION OF A PREFERRED EMBODIMENT

Referring now to the drawings wherein like reference characters designate like parts throughout the several views, FIG. 1 shows a dialyzing membrane 10, which is shown in a distended state. It will be clear that the membrane is sealed to the dialyzing chamber 12 around its periphery so as to restrict the flow of fluid from the blood portion 14 to the dialysate portion 16 to flow only through membrane 10.

Blood from the patient to be dialyzed is applied to blood inlet 18, passes under membrane 10, and exits chamber 12 through blood outlet 20. The dialysate is applied through dialysate inlet 22, passes over membrane 10, and out the dialysate outlet 24. FIG. 1 shows what is considered to be a cross-current dialyzing system which is characterized by non-parallel flow of the blood and dialysate supplied to the membrane 10. An example of co-current, or parallel blood flow, can be seen by reference to FIG. 2.

Because the blood inlet pressure is determined by the patient's blood pressure, arterial conditions and connection, and the blood output pressure is determined by the venous condition and connection, it is generally not considered acceptable to attempt to control blood pressure on membrane 10. In a single pass hemodialysis system, dialysate is supplied to the membrane 10, and is, then, drained off to be disposed of. In prior art dialyzers, because the dialysate was drained off, there was very low dialysate solution pressure which caused a relatively high transmembrane pressure, in many instances 100 mmHg or more. In the present invention, the dialysate solution pressure is maintained at a higher level because of the restriction on dialysate output flow caused by clamp 26. Thus, by restricting the flow through the dialysate outlet 24 by increasing the pressure of clamp 26 on the outlet line, the dialysate solution pressure in the dialysate portion 16 of chamber 12 can be raised to a level approaching the blood pressure in blood portion 14 of the dialysis chamber 12. The dialysate solution pressure is never raised above the blood pressure, such that, in the event of a membrane rupture, blood will always flow into the dialysate solution, and prevent the flow of dialysate into the patient's body. In the embodiment shown in FIG. 1, a differential, or transmembrane, pressure indicator 28 is depicted, which senses the difference in pressure between blood portion 14 and dialysate portion 16 of chamber 12.

During operation, the patient would be connected in conventional fashion to the dialyzer which has been equipped with a high flux membrane 10. Dialysate flow through the dialyzer chamber 12 would be initiated in a normal manner, and the operator would gradually restrict the dialysate output flow by tightening clamp 26. When the transmembrane pressure drops to indicate the acceptable level of ultrafiltration for the patient (generally between 0 and 30 mmHg), adjustment of the clamp 26 would be terminated. The operation of the high flux membrane 10 will permit passage of "middle molecules", with a size on the order of 300 to 2000 daltons, at a rate so as to significantly reduce the level of such middle molecules in the patient. Unlike the closed loop system, because fresh dialysate is entering the dialyzing chamber all the time, the maximum clearance (or rate of solute transfer across the membrane) will be maintained at a high level because of the great solute concentration difference between the dialysate and the patient's blood. However, the ultrafiltration of the patient will be maintained at a very low level because of the low transmembrane pressures involved. Thus, not only is there an effective removal of conventional small molecular weight solutes (metabolites such as urea and creatinine which have molecular weights less than 300 daltons) with precise control of ultrafiltration of the patient, but there will also be a significant removal of middle molecules, which combination has heretofore been impossible.

Tests have indicated that dialyzers operating in the co-current mode will be most effective with the inventive method of dialyzing patients. Because there is some pressure drop between the blood inlet 18 and the blood outlet 20 (and, similarly, between the dialysate inlet 22 and dialysate outlet 24), if membrane 10 is freely-mounted (that is, restricted around its periphery), it will distend, such that the transmembrane pressure is essentially equal at all points on the membrane. Thus, while there may be a pressure drop between the input and output, the membrane will distend, such that the transmembrane pressure (between the blood and dialysate) will be constant. This is believed to indicate that a dialyzer operating in the co-current mode, as in FIG. 2, will be most effective.

FIG. 2 also discloses an automated transmembrane pressure regulation system which will greatly facilitate the operation of a dialyzer in accordance with the applicant's inventive method. A means for maintaining transmembrane pressure is shown in the dotted line block 32 of FIG. 2. This may include a means for sensing transmembrane pressure, such as pressure sensor 30, which provides an output 34 to pressure control means 36, which controls the actuation of dialysate outlet valve 38. In operation, if the pressure sensor 30 senses a transmembrane pressure which is higher than the decided optimum amount for that patient (generally between 0 and 30 mmHg), it will provide an output 34 to pressure control means 36, which will close outlet valve 38 by a small amount. This has the effect of restricting the outlet flow of the dialysate, causing the pressure in dialysate portion 16 to increase, more closely approaching the higher pressure in blood portion 14, and thus, reducing the transmembrane pressure to the required level.

Although the invention has been described relative to a specific method and apparatus embodiment thereof, it is not so limited, and many modifications and variations thereof will be readily apparent to those skilled in the art of hemodialysis in light of the above teachings. For example, a mechanical system could be utilized to actuate the output valve. Other possibilities include electronic sensors to monitor and record transmembrane pressure, as well as provide the required output to the pressure control means. Varying flow rates of bllod and dialysate can be utilized, depending on the individual patient's needs. As shown in FIGS. 1 and 2, the operation could either be monitored and controlled manually, or automatically. As the required high flux membranes are improved, it may be medically acceptable to have a transmembrane pressure of zero, or even slightly negative (dialysate solution pressure greater than blood pressure), although this would depend upon membrane technology, ensuring that there can be no ruptures in the membrane which would cause contamination of the patient's blood with dialysate solution. It will be clear that the applicant's method of utilizing a single pass dialyzer with a high flux membrane at very low transmembrane pressures can easily be modified to provide a brief period of high transmembrane pressure (by adjustment of pressure control means 36) in order to rapidly ultrafilter a patient initially and, then, later continue dialysis at a very low ultrafiltration rate. This process has been found beneficial for patients suffering from blood pressure anomalies. Thus, the applicant's method and modification of existing single pass dialyzers will facilitate a step ahead for hemodialyzers which provide the gift of life to patients suffering from renal failure.

It is, therefore, to be understood that within the scope of the appended claims, the invention may be practiced otherwise than as specifically described.

The embodiments of the invention in which an exclusive property or privilege is claimed are defined as follows:

1. A method of single pass hemodialysis for removal of metabolites from the blood of a patient including middle molecules of a size on the order of 300 to 2000 daltons, comprising the steps of:
providing a single pass hemodialyzer with a freely-mounted membrane having an ultrafiltration coefficient of at least 20 ml m$^{-2}$ hr$^{-1}$ mmHg$^{-1}$;
connecting said patient to said single-pass hemodialyzer in a conventional manner; and
operating said hemodialyzer with a transmembrane pressure of between 0 and 30 mmHg to reduce ultrafiltration of the patient.

2. In a single-pass hemodialyzer for hemodialysis of a patient, said dialyzer including a freely-supported dialyzing membrane such that the patient's blood is circulated past one side of the membrane and a dialyzing solution is circulated past the other side of the membrane, there being a transmembrane pressure caused by the blood pressure exceeding the dialysate pressure, said improvement comprising:
said membrane is a high flux membrane having an ultrafiltration coefficient of at least 20 ml m$^{-2}$ hr$^{-1}$ mmHg$^{-1}$ and a reflection coefficient of about zero for solutes having a molecular weight up to 2000 daltons; and means for maintaining the transmembrane pressure at between 0 and 30 mmHg at least one point on the membrane.

3. The improvement of claim 2, wherein said dialyzer is a co-current dialyzer and said means for maintaining comprises:

means for sensing the transmembrane pressure; and pressure control means, responsive to said means for sensing, for adjusting dialysate solution output pressure to a level at which said transmembrane pressure is between 0 and 30 mmHg.

4. The improvement of claim 2, wherein said dialyzer is a cross-current dialyzer and said means for maintaining comprises:

means for sensing a single transmembrane pressure; and pressure control means, responsive to said means for sensing for adjusting dialysate solution output pressure to a level at which said transmembrane pressure is between 0 and 30 mmHg.

5. The improvement of claim 2, wherein said dialyzer is a co-current dialyzer and said means for maintaining comprises:

transmembrane pressure indicator means for indicating to an operator the transmembrane pressure; and clamp means, operable by said operator, for increasing dialysate output pressure.

* * * * *